United States Patent [19]

Schunck et al.

[11] 4,101,221
[45] Jul. 18, 1978

[54] PROCESS FOR THE PHOTO-OPTICAL MEASUREMENT OF THE ABSORPTION BEHAVIOR OF SOLID, LIQUID AND GASEOUS MEDIA

[75] Inventors: Günter Schunck; Albert Randwo, both of Bruchköbel, Fed. Rep. of Germany

[73] Assignee: Leybold-Heraeus GmbH & Co. KG, Cologne, Fed. Rep. of Germany

[21] Appl. No.: 780,400

[22] Filed: Mar. 23, 1977

[30] Foreign Application Priority Data

Apr. 2, 1976 [DE] Fed. Rep. of Germany ....... 2614181

[51] Int. Cl.$^2$ .............................................. G01N 21/22
[52] U.S. Cl. .................................... 356/205; 250/343; 250/351
[58] Field of Search ............... 250/343, 351; 356/204, 356/205

[56] References Cited

U.S. PATENT DOCUMENTS

| 2,679,185 | 5/1954 | Atwood | 250/343 |
| 3,560,098 | 2/1971 | Witte et al. | 356/205 |
| 4,008,394 | 2/1977 | Risgin et al. | 250/343 |

Primary Examiner—John K. Corbin
Assistant Examiner—R. A. Rosenberger

Attorney, Agent, or Firm—Burgess, Dinklage & Sprung

[57] ABSTRACT

A process and apparatus for the photo-optical measurement of the absorption behavior of solid, liquid and gaseous media. The analysis medium and a comparison medium are exposed to two light beams. The light beams are broken up by a chopper means into a periodical sequence of light pulses and the measured difference of the beam attenuations in the analysis medium and comparison medium is evaluated in a circuit which is adjustable with regard to the intensity of the radiation from the optical light source and the sensitivity of the light receiver. The light pulses are divided by defined variation of their intensity into two different pulse series of which one series comprises measuring light pulses and the other series comprises control pulses. The evaluation of the measuring light pulses is periodically interrupted by the control pulses for a relatively short time period and the actual value of the control pulses is compared with a standard value during said time period, and the circuit is adjusted during said time period in accordance with the difference between the actual value and the standard value so that said difference is decreased to as small a value as possible, whereupon the following measuring light pulses are again evaluated for the purpose of a measurement.

9 Claims, 7 Drawing Figures

PROCESS FOR THE PHOTO-OPTICAL MEASUREMENT OF THE ABSORPTION BEHAVIOR OF SOLID, LIQUID AND GASEOUS MEDIA

BACKGROUND

The invention relates to a process for the photo-optical measurement of the absorption behavior of solid, liquid and gaseous media, especially in the photometric analysis of gases by infrared rays, by exposing the medium being analyzed and a standard medium to light beams broken up by a chopper device into a periodical succession of light pulses, and evaluating the measured difference between the beam attenuations in the tested medium and the standard medium in circuitry which is adjustable as regards the radiation intensity of the optical light source and the sensitivity of the light receiver.

The use of intermittent measuring light beams is common in the photo-optical measuring art. The expression, "light modulation," is also used, and the devices used for this purpose are referred to as choppers. The light modulation is performed mainly for the purpose of separating the actual measuring signal from noise signals, the noise signal having a different frequency than the measuring signal. Also, some common detectors, especially gas detectors using micro-flow sensors, are suitable only for the reception of intermittent light radiation.

The invention finds application mainly in the field of gas analysis through the determination of the absorption of infrared radiation. Such processes and apparatus are the state of the art (German "Auslegeschrift" No. 1,296,839 and 1,698,218).

Light choppers or modulators for photometers are known in a great number of versions. In most cases they involve an electric motor on whose shaft there is fastened a chopper wheel provided with apertures. In the known choppers the apertures are of the same size and uniformly distributed over the circumference of the chopper wheel, so that a pulse sequence of constant intensity is formed, assuming that the conditions of measurement and the medium being analyzed are the same (German "Auslegeschrift" No. 1,946,211, FIG. 2).

In photometers using infrared radiators it is common to check and, if necessary, adjust the sensitivity by means of a defined beam attenuation using calibrating gas or a test diaphragm in the measuring channel. This is necessary because, among other reasons, changes of intensity in the radiation of the infrared source and in the sensitivity of the measuring light receiver are virtually unavoidable, so that correction of the measuring apparatus is necessary at more or less regular intervals of time. It is disadvantageous that, in the known apparatus, a zero check or adjustment is first required before making the sensitivity check, the time constant for the indication of the correction being the same as or similar to that of the actual measuring signal. The requirement that the absorption in the medium being analyzed be zero for the zero level adjustment signifies an often unpleasant limitation in apparatus that are in constant use. For this purpose the medium being analyzed has to be removed and the radiation in the analysis medium has to be given a defined attenuation. In this case the reading must be equal to a given calibration value. If it is not, the sensitivity has to be readjusted. In one known apparatus, a pivotable screen has to be swung into the standard channel for the purpose of the adjustment (German Pat. No. 2,042,727). Such measures must generally be performed separately from the measurement operation and consequently they are time-consuming. If the sensitivity varies undetected during operation, the readings will contain an error.

THE INVENTION

The invention is addressed to the problem of improving an apparatus of the kind described above such that the influence of changes in light source intensity and in the sensitivity of the light receiver will be eliminated virtually entirely, so that the stability of the measuring signal will be substantially increased and any drifting or any effect of temperature on the light source and receiver will be reduced. Furthermore, regular tests for checking the zero level are to be necessary only at substantially longer time intervals than hitherto.

The solution of the above-stated problem is accomplished by the present invention in the process described above by the fact that the light pulses are divided on the basis of a defined variation of intensity into two different pulse series, of which one series is a series of measuring light pulses and the other is a series of control pulses; that the evaluation of the light pulses as measuring light pulses is periodically interrupted by the control pulses for a brief span of time, during which the actual value of the control pulses is detected and compared with a standard value, and that the adjustment of the circuitry in accordance with the difference between the actual and standard values of the control pulses is performed such that this difference is as small as possible, whereupon the succeeding measuring light pulses are again subjected to evaluation for the purpose of a measurement.

Since usually the chopper frequency ranges from about 5 Hz to about 500 Hz and above, depending on the nature of the gas detector or light receiver used, a speed of about 60 to 6000 revolutions per minute is required when a rotating chopper disk of, for example, five holes is used. If the intensity variation in accordance with the invention is created on the circumference of the chopper wheel, the adjustment is performed automatically and entirely imperceptibly during the extremely short time span of a portion of the time required for one revolution. The correction is thus performed periodically at such brief intervals that changes in the intensity of the radiator or drifting of the receiver are almost completely corrected. The stability of the measuring signal is thereby substantially improved. Furthermore, no interruption of the measurement is necessary for the performance of a control measurement or for adjustment. Neither is it necessary to remove the medium being analyzed.

The invention relates also to an apparatus for the performance of the process described above. It consists of an optical radiation source, a test absorption cell, a comparative absorption cell, a chopper for the light rays passing through both absorption section cells, at least one light receiver, and a circuit for the indication of the measured value, equipped with at least one adjusting means for the compensation of variations of the radiation intensity of the optical radiation source and of the sensitivity of the light receiver. Such apparatus is characterized in accordance with the further invention by the fact that the chopper device is provided at least in the area of one absorption cell with holes or hole groups of varying ability to admit light, which periodically pass through the light beam, and that in the circuitry following the light receiver a comparing circuit is provided for comparing the actual and standard values of the control pulses, and a regulating amplifier connected to the output of the comparing circuit, a phasing system synchronized by the receiver signals, and a plurality of circuit means controlled by the phasing system, by which the measuring light pulses are fed alternately and periodically to an indicator means and the control pulses are fed alternately and periodically to the comparing circuit and to the phasing system. Such a solution affords the constructional requirements and advantages for the performance of the process of the invention.

The uninterrupted and periodical switching back and forth between measurement and calibration can be accomplished circuit-wise in an especially simple manner by connecting the input of the comparing circuit to the output of a phase-selective detector for rectification of the pulse sequence, and connecting the phasing means to the output of another phase-selective detector to reverse the polarity of the pulse sequence beyond a phase angle of 90° and again reversing the polarity after 270°, the phase-selective detectors being modulated by the phasing means.

The defined variation of the intensity between the pulse sequences can be positive or negative, i.e., the control pulses can be either amplified above or attenuated below the measuring light pulses. It is only necessary to produce an intensity change that is easily evaluated by the following circuit, and which can be converted to a defined signal magnitude. Changes of intensity between 20 and 50% between the one pulse sequence and the next have proven to be entirely practical. It is only necessary that a definite relationship, unaffected by any other parameters, exist between the detector signal containing the defined variation and the unchanged detector signal, on the one hand, and the detector signal produced by the medium being analyzed on the other hand.

Especially advantageous and simple circuitry for the embodiment of the teaching of the invention can be achieved by making the chopper means to consist of a uniformly driven, rotating wheel having two rows of holes or groups of holes, the one row being associated with the test cell and the other row with the standard absorption section, and by providing in each row at least one hole or group of holes with a cross section differing from the other holes or groups of holes. By varying the cross-sections of the holes within a series of holes the corresponding amplification or attenuation of the pulse is brought about, since each hole acts as a diaphragm. The holes can be arranged in pairs, i.e., they can be placed beside one another radially, so that the absorption test cell and the standard absorption cell will simultaneously receive the optical radiation. It is simpler for the signal processing, however, if the holes of the two rows are offset from one another, so that the radiation strikes the test and the standard cells alternately.

It is likewise possible to provide holes or groups of holes of different aperture cross sections in the area of only one absorption cell—for example the standard cell. It is especially desirable as regards signal processing, however, if a defined variation of the intensity of the pulses takes place both on the measuring side and on the comparison side.

BRIEF DESCRIPTION OF THE DRAWINGS

An example of the embodiment of the invention and variants of the chopper means and the manner of operation thereof will be further described herewith with reference to the appended FIGS. 1 to 7.

DETAILED DESCRIPTION OF THE PREFERRED EMBODIMENTS

Figure 1:
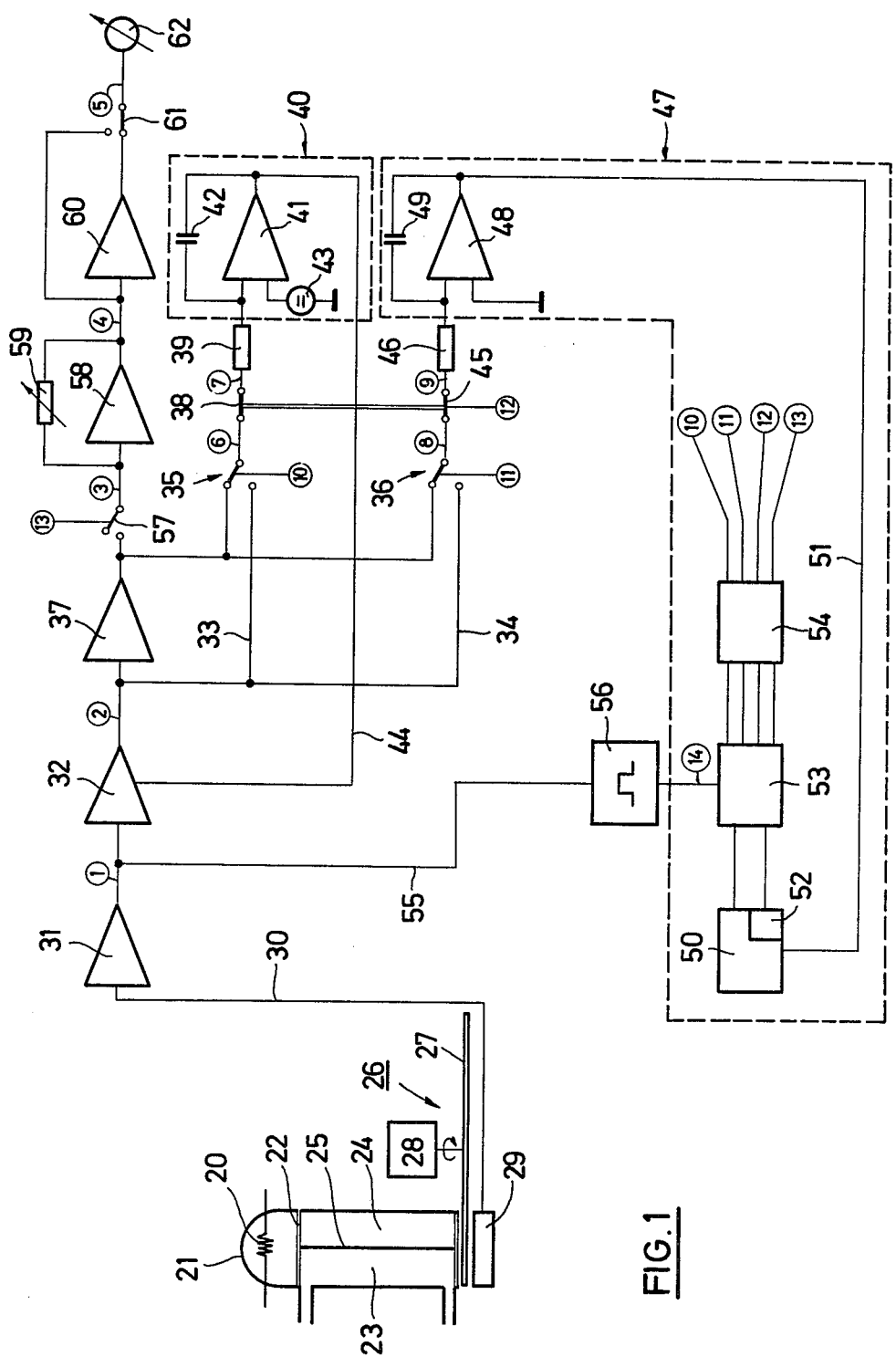
FIG. 1 is a block circuit diagram of an infrared gas analyzer whose output is connected to a measuring and regulating system.

In FIG. 1, 20 is a radiation source consisting of a virtually black radiator whose temperature is about 700° C. The radiation source is associated with a reflector 21 which reflects the infrared radiation towards a window 22 transparent to infrared light. Below the window is a system of two absorption chambers or cells, namely the test absorption cell 23 and the standard absorption cell 24, between which there is a partition 25. In the present case the two absorption cells consist of a common cylindrical tube divided by the partition into the test cell and the standard cell. It is quite possible, however, to construct the absorption cells in the form of two separate cylinders. Below the absorption cells is chopper means 26 which consists of a flat chopper wheel 27 and a driving motor 28. On the other side of the chopper wheel 27 there is provided a light receiver 29 with which the light emerging from the test and standard chambers is measured. As a variant of the construction represented, it is also possible to dispose the chopper wheel 27 above the absorption cells.

The light receiver can be one of a variety of types. For example, it can be a semiconductor detector selectized by optical pass band filters, or a gas detector which has been reduced to a small time constant by the use of a flow detector (anemometer), such as the one described in the dissertation of G. Schunck of Oct. 9, 1974, without appreciable loss of resolution. Fundamentally, infrared detectors of a relatively large time constant are also usable, although a detector having a fast response considerably facilitates the signal processing.

Figure 6:
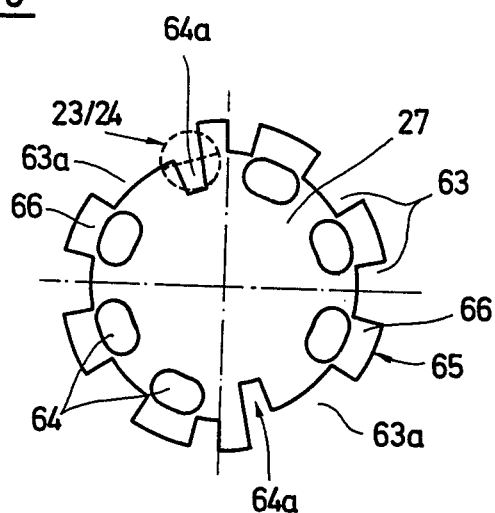
FIG. 6 is a plan view of a variant of the chopper wheel of FIG. 3.
Figure 7:
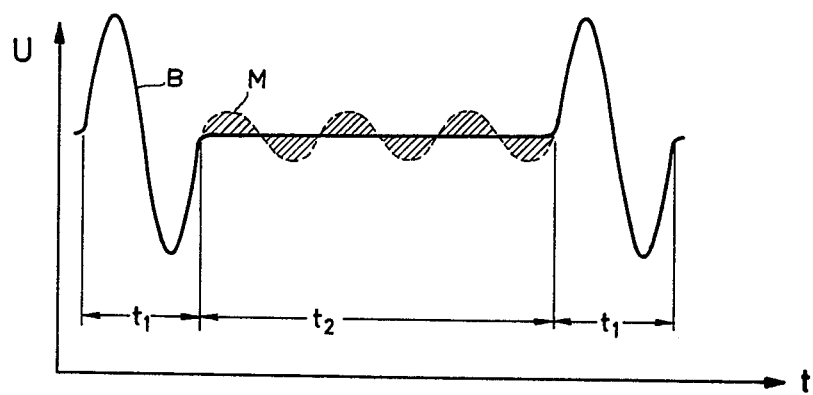
FIG. 7 shows the signal diagram obtained with the chopper wheel of FIG. 6 in the same manner as the one in FIG. 4.

In the present case, a chopper wheel in accordance with FIG. 6 is used, so that the signal shown in FIG. 7 is at the output of the light receiver 29. The signal is fed through a conductor 30 to a preamplifier 31, and from there to a control amplifier 32. The control amplifier is connected by lines 33 and 34, respectively, to two phase-selective detectors 35/37 and 36/37, which are 90° apart, and which consist each of one switcher, 35 and 36, respectively, and one inverter 37.

The output of the phase-selective detector 35/37 is switched by a switcher 38 and a resistor 39 to a comparison circuit 40 whose most important part is a sample-and-hold integrator formed by an amplifier 41 in conjunction with the switcher 38 and a condenser 42. The input of the amplifier 41 is connected to a signal generator 43 which produces a direct-current voltage and provides the standard for the intensity of the control pulses. The output of the comparison circuit 40 is fed back through a conductor 44 to the regulating amplifier 32.

The output of the phase-selective detector 36/37 is connected through a switcher 45 and a resistor 46 to a phasing system 47 to which likewise belongs a sample-and-hold integrator which is formed of an amplifier 48 in conjunction with the switcher 45 and a condenser 49.

Also part of the phasing system 47 is a phase lock loop circuit 50 to which the output of amplifier 48 is connected through a conductor 51. The phase lock loop circuit 50 contains an integrated, voltage-controlled oscillator 52. Its output is connected to a counter 53 embodied in the form of a Johnson counter, whose output is connected to a decoder 54. The output of the preamplifier 31 is connected by a conductor and a pulse shaper 56 also to the counter 53. The outputs of the decoder 54 are provided with the circled reference numbers 10, 11, 12 and 13, and are connected (not shown in FIG. 1) to the elements provided with the same reference numbers in the upper portion of the circuit diagram.

The output of the inverter 37 is connected by a switcher 57 to an amplifier 58 which permits selection of range through a parallel-connected variable resistor 59. The output of the amplifier 58 is connected to an additional phase-selective detector consisting of an inverter 60 and a switcher 61. The switcher 61 output is connected to an indicator means 62 which serves for the indication of the measured value. Smoothing devices for the smoothing of the ripple in the signal have been omitted for the sake of simplicity.

The system represented in FIG. 1 operates in the following manner, which will be described also with reference to FIG. 2: The signal emitted by the light receiver 29, after preamplification, has at point (1) a curve which consists of a sine wave of great amplitude and three sine waves of small amplitude, as represented in FIG. 7, on the basis of the geometry of the chopper wheel 27, as represented in FIG. 6, which is used. The curve portion of great amplitude is referred to also as a burst signal and in FIG. 2 it is indicated at (1) by the letter B. The burst signal forms what are referred to as the control pulses. The curve portion of small amplitude is used for the actual measurement and is identified as M at (1) in FIG. 2. The mesuring signals form what are called the measuring light pulses. At the output of the control amplifier, the curve of the signal at (2) has a shape substantially similar to the shape at (1). This signal appears at the lower contacts of the switchers 35 and 36 and, on account of the inverter 37, it appears as an inverse signal at the upper contacts of the switchers 35 and 36. Due to the phase-controlled periodical switching action of the switchers 35 and 36 by the control pulses which are 90° out of phase as represented at (10) and (11) in FIG. 2, the rectified pulsating wave shape is produced from the wave shape (2), following the switcher 35. On account of the 90° dephased operation of the switcher 36, the signal (8) is formed from signal (2) and has very steep flanks at the crossover points. The signal series (6) and (8) are then interrupted time-wise by the simultaneously operated switchers 38 and 45 in an entirely specific manner. By a pulsed control voltage represented at (12) in FIG. 2, whose length corresponds precisely to the length of the burst signal, the pulse series (6) and (8) are blanked time-wise such that the pulse series (7) and (9) are formed, which contain only the part that corresponds to the burst and control signals, respectively.

The pulse sequence (7) is then integrated by means of the sample-and-hold integrator 38/41/42 of comparison circuit 40, and compared with the output of the standard signal generator 43. If there is no difference, the gain of the control amplifier 32 remains unchanged. If a difference between the actual value and the standard value is found, the control amplifier 32 is modulated via line 44 such that the difference in the comparison circuit 40 will have a minimum value, especially the value zero.

Figure 2:
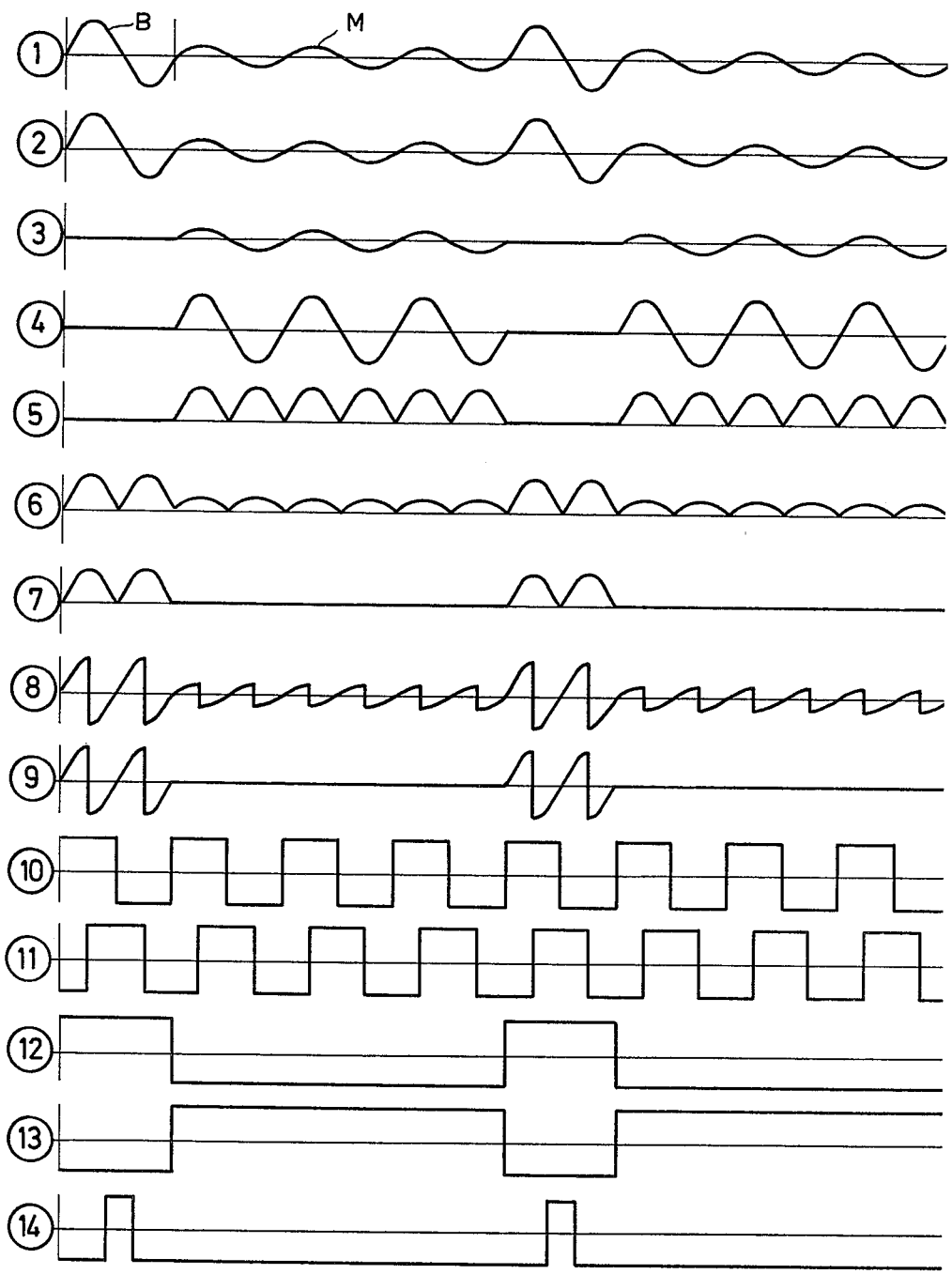
FIG. 2 is a signal diagram of the signals in the individual lines at points designated by the circled numerals 1 to 14.

The pulse series (9) is transformed by means of the sample-and-hold integrator 45/48/49 of the phasing system 47 through the phase lock loop circuit 50, the counter 53 and the decoder 54, on the basis of the synchronization through the pulse former 56 into a total of four pulse series which correspond to the curves (10) to (13) of FIG. 2. Details concerning blocks 50, 53 and 54 are in the state of the art, so that there is no need to describe them here.

It can be seen that the pulse series (13) is the inverse of the pulse series (12), so that the switcher 57 is opened whenever the switchers 38 and 45 are closed, and vice versa. From this it is apparent that the signal series after the switcher 57 at point (3) contains only those signals which correspond to the actual measuring light signals M. These are amplified in the amplifier 58, so that they have the shape represented in FIG. 2. Rectification is performed by the phase detector 60/61, so that at (5) there appears a (pulsating) direct current, which can be made visible by the indicating means 62 in the form of a read-out.

It can be seen that merely through the deliberate differentiation of the pulses into control pulses and measuring light pulses, plus the above-described circuitry, separation into two different pulse series is possible, one of which is used for the automatic and periodical calibration of the circuitry and the other is used for the formation of the measuring signal.

Figure 3:
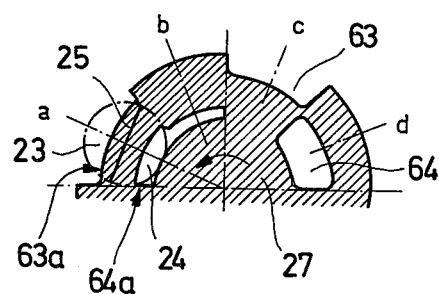
FIG. 3 is a plan view of an embodiment of a chopper wheel.
Figure 4:
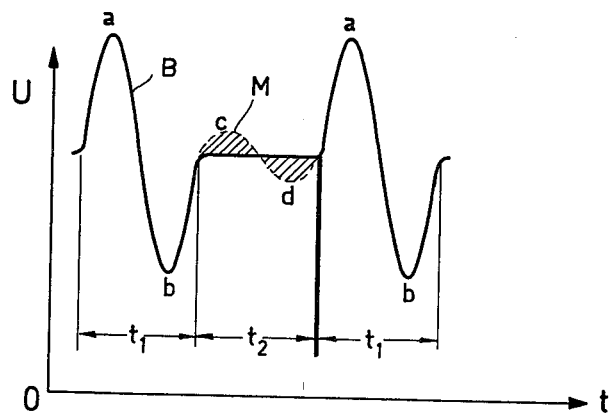
FIG. 4 is a diagram of the receiver signal produced by the chopper wheel of FIG. 3.

In FIG. 3 there is shown a chopper wheel 27 and its position in relation to the test cell 23 and the standard absorption chamber 24 and partition 25. The chopper wheel 27 has on its semicircumference four different sectors, a, b, c and d. The configuration of the individual sectors is repeated circumferentially, in the same sequence. The chopper wheel is cross-hatched for the sake of clarity. The varying masking or attenuation of the beam at positions a and b on the one side and c and d on the other, causes the signal voltage produced by the light receiver to appear as represented in FIG. 4. The curve for time interval $t_1$ indicates the burst signal B. The surface area within curve M during time interval $t_2$ is a measure of the intensity of radiation absorbed in the medium being analyzed. Within this time interval takes place the actual measurement of the unknown object on the basis of the circuit in FIG. 1.

Figure 5:
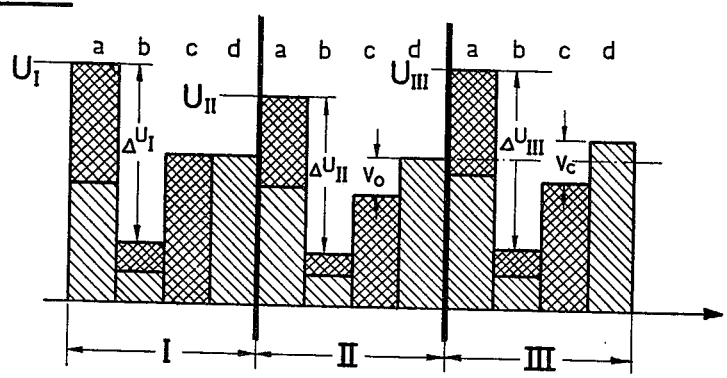
FIG. 5 is a comparison of the individual signal components in three different cases: without absorption in the analysis medium, with absorption in the analysis medium but without correction, and with absorption in the analysis medium and with correction of the circuitry.

For better understanding of the process, the signals based on the intensity curves of FIG. 4 are represented in FIG. 5 by surfaces, the single cross-hatched surface being a measure of the intensity of the radiation from the standard absorption cell. The representation in the left part I corresponds to a system in accordance with FIG. 1 in which there is no analysis medium in the test cell. The sum of the measured signal portions therefore corresponds, in position a of the chopper wheel, to the value $U_I$. When position b of the chopper wheel passes by, the signal for the sum of the measured intensities in both of the absorption cells has a much lower value due to the greater masking. The difference of the two sums in positions a and b has the value $\Delta U_I$. This is the value which serves hereinafter as the basis for the operation of the control amplifier 32. In position c, the standard absorption cell 24 is entirely masked; all that is measured is the radiation from the test cell, which, of course, is identical to the radiation from the standard cell when sector d passes through.

The center part II characterizes a state in which an analysis medium having an absorption of 25% is in the test cell. The signal of the sum of radiation intensities from both absorption cells consequently amounts to no more than the value represented as $U_{II}$ when sector a of the chopper wheel passes through. The same applies proportionately to sector b. The difference of the two sums in positions a and b now has no more than the value $\Delta U_{II}$. The intensity signal produced when sector c passes through will, of course, have a value reduced by 25%. The difference in relation to the intensity signal from the (unchanged) standard absorption chamber will be the actual measured value $V_0$. This value can be correct, but it can also contain a measuring error if, for example, the radiation intensity of the radiation source 20 and/or the sensitivity of the light receiver 29 have changed due to external influences. The middle part II of the diagram shows the conditions without corrective intervention.

When the system of the invention is applied, the conditions represented in the right part III of the diagram will establish themselves automatically. In this case, too, an analysis medium having an absorption of 25% is in the test cell. On the basis of the comparison that has been made of the difference $\Delta U_{III}$ of the sum of the signal components between the passages of sectors a and b of the chopper wheel with a given standard value (standard value signal generator 43), a corresponding intervention into the control amplifier 32 is performed through the comparison circuit 40 and the conductor 44, so as to bring the above difference $\Delta U_{III}$ back up to the value $\Delta U_I$, i.e., $\Delta U_{III} = \Delta U_I$. This results in a corresponding proportional amplification of the signals from the standard absorption cell on the one hand and the test cell on the other, the difference also being amplified proportionally to a corrected value $V_c$. Independently of the fact that in this manner every influence on the accuracy of measurement is compensated without delay, a linearization effect is additionally produced in the manner described with regard to the dependence of the test signal upon the test absorption. This dependence can be represented as an e function, i.e., as the concentration of the absorbing analysis medium increases, the signal does not increase to the same extent. The ideal would be a linear relationship, which hitherto has not been achievable on the basis of the physical circumstances. With the process of the invention, the additional advantage is achieved that the dependence of the measuring signal on the concentration is changed in the direction of greater linearity.

Since the measuring signal from the unknown specimen is often very small, but the defined beam attenuation can be made comparatively great, it is desirable, for the achievement of a great signal-to-noise ratio, to select the largest possible ratio of $t_2:t_1$. FIG. 6 shows a chopper wheel 27 which produces a $t_2:t_1$ ratio of 3. The chopper wheel shown uses a 50% intensity change for the adjustment. The curve of the output signal from light receiver 29 resulting therefrom is represented in FIG. 7 in the same manner as the curve in FIG. 4.

The chopper wheel of FIGS. 3 and 6 consists of a uniformly drivable, rotating disk, made for example of a metal such as aluminum, for example, having two rows of holes 63–63a and 64–64a, respectively, the one row 63–63a being associated with the test cell 23 and the other row 64–64a with the standard cell 24. In each row there is at least one hole 63a and 64a, respectively, which has a cross section that differs from the other holes 63 and 64, respectively. It is especially desirable to arrange the sequence of the holes such that the rotational symmetry of the chopper wheel is preserved, so as to avoid imbalance.

In the configuration shown in FIG. 6, a plurality of successive holes in a row 63 or 64 form a set which is followed by a hole of different cross section 63a or 64a, respectively. It would also be possible, however, to dispose the holes of variant cross section in sets and to adapt the circuitry of FIG. 1 accordingly.

In the configuration shown in FIG. 6, the outer row of holes 63,63a crosses over the edge 64 of the chopper wheel 27, so that radial projections 66 are formed. At two points on the circumference, namely at 63a, one of the projections is entirely removed, while in the inner row of holes, two holes 64a have a cross section that is smaller than that of holes 64.

What is claimed is:

1. In a process for the photo-optical measurement of the absorption behavior of solid, liquid and gaseous media, by exposing the analysis medium and a comparison medium to two light beams and breaking up the light beams by chopper means into a periodical sequence of light pulses and evaluating the measured difference of the beam attenuations in the analysis medium and comparison medium in a circuit which is adjustable with regard to the intensity of the radiation from the optical light source and the sensitivity of the light receiver, wherein the improvement comprises dividing the light pulses by defined variation of their intensity into two different pulse series of which one series comprises measuring light pulses and the other series comprises control pulses, periodically interrupting the evaluation of the measuring light pulses by the control pulses for a relatively short time period and comparing the actual value of the control pulses with a standard value during said time period, and adjusting the circuit during said time period in accordance with the difference between the actual value and the standard value decreasing this difference to as small a value as possible, and evaluating the following measuring light pulses for the purpose of a measurement.

2. In an apparatus for the photo-optical measurement of the absorption behavior of solid, liquid and gaseous media, of the type having an optical radiation source, a test cell, a standard absorption cell, chopper means for breaking up light beams passing through both cells into a periodic sequence of light pulses, at least one light receiver, and a circuit for the indication of the measured value and adjustable for compensating for changes in the radiating intensity of the optical radiation source and in the sensitivity of the light receiver, wherein the improvement comprises: the chopper means including at least one set of holes having alternatively different light admitting ability and disposed in the range of each cell to periodically pass through the light beams through the cells to define light pulses divided by defined variation of their intensity into two different pulse series of which one series comprises measuring light pulses and the other series comprises control pulses having a relatively short time duration, and the circuit comprises a comparison circuit connected to the output of the light receiver for comparing the actual value of the control pulses to a given standard value and a regulating amplifier controlled by the comparison circuit for effecting adjustment of the circuit to decrease the difference between the actual and standard values of the control pulses during the time duration, a phasing circuit synchronized by the control signals, and a plurality of circuits controlled by the phasing circuit for alternately periodically feeding the control pulses during each time duration to the comparison circuit and to the phasing circuit and feeding the measuring light pulses to be indicating after each time duration.

3. The apparatus according to claim 2, wherein the circuit comprises a phase-selective detector connected to the comparison circuit for the rectification of the pulse sequence and another phase-selective detector connected to the phasing circuit for reversing the polarity of the pulse sequence with a phase angle of 90°, the phase-selective detectors being driven by the phasing circuit.

4. The apparatus according to claim 3, wherein the phasing circuit comprises a phase lock loop circuit, a counter and a decoder with four outputs the pulses at two outputs out of phase by 90° and connected to the phase selective detectors, and the pulses at the other two outputs being inverse to one another and switches connected to the other two outputs for the blanking of the measuring light pulses during each time duration and the control pulses after each time duration.

5. The apparatus according to claim 4, further comprising a pulse shaper, an amplifier for feeding signals from the light received to the pulse shaper and wherein the counter receives signals from the pulse shaper.

6. The apparatus according to claim 2, wherein the chopper means comprises a uniformly drivable, rotatable chopper wheel having two rows of holes, one row being associated with the test cell and the other row with the standard absorption cell and that in each row at least one hole has a cross section deviating from that of the other holes.

7. The apparatus according to claim 6, wherein the cross sections of the holes differ from one another by at least 20%.

8. The apparatus according to claim 6, wherein the outer row of holes cuts across the edge of the chopper wheel to form radial projections and that at least at one point of the circumference one of the projections is at least partially removed, and that in the inner row of holes the cross section of at least one of the holes is reduced in the vicinity of the removed projection.

9. The apparatus according to claim 6, wherein the hole arrangement is disposed rotationally symmetrical on the chopper wheel.

* * * * *